United States Patent [19]

Nisato et al.

[11] 4,409,228

[45] Oct. 11, 1983

[54] ANOREXIANT AMINOPIPERIDINES INTERMEDIATES THERETO AND DRUGS CONTAINING SAME

[75] Inventors: Dino Nisato, Pavia; Paolo Carminati, Milan, both of Italy

[73] Assignee: Sanofi, France

[21] Appl. No.: 327,022

[22] Filed: Dec. 3, 1981

Related U.S. Application Data

[63] Continuation of Ser. No. 159,603, Jun. 16, 1980, abandoned.

[30] Foreign Application Priority Data

Jun. 21, 1979 [FR] France ................................ 79 15974

[51] Int. Cl.³ .................. A61K 31/445; C07D 401/04
[52] U.S. Cl. ................................... 424/267; 546/193; 546/194; 546/244
[58] Field of Search ................ 546/193, 194; 424/267

[56] References Cited

FOREIGN PATENT DOCUMENTS 738495  8/1943  Fed. Rep. of Germany .

OTHER PUBLICATIONS

Schatz, V. In *Medicinal Chemistry*, 2nd Ed. (Burger, Editor), Interscience, New York, 1960, pp. 78–79.

Stern, P., *Arch. Exp. Pathol. Pharmacol.*, 1942, 199, 251–264.

Cerkovnikov, E., et al., *Chem. Ber.*, 1941, 74, 1648–1657.

*Primary Examiner*—Richard A. Schwartz
*Attorney, Agent, or Firm*—Schroeder, Siegfried, Vidas & Arrett

[57] ABSTRACT

The present invention relates to novel 4-amino-1-(2-pyridyl)piperidines with anorexiant action, of formula:

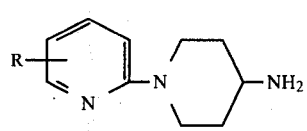

in which R represents hydrogen, a halogen, a methyl group, a trifluoromethyl group, a lower alkoxy group, a trifluoromethoxy group, a 2,2,2-trifluoroethoxy group, a lower alkylthio group, a trifluoromethylthio group, a possibly substituted phenoxy group or a possibly substituted phenylthio group; to salts thereof; to a process for preparation thereof; to drugs containing same; and to intermediate products in the synthesis thereof.

11 Claims, No Drawings

ANOREXIANT AMINOPIPERIDINES INTERMEDIATES THERETO AND DRUGS CONTAINING SAME

This is a continuation, of application Ser. No. 06/159,603, filed June 16, 1980, now abandoned.

The present invention relates to novel aminopiperidines having an anorexiant activity, to a process for preparation thereof, to novel intermediates used in said process, as well as to drugs containing these aminopiperidines as active ingredients.

More particularly, the present invention relates to 4-amino-1-(2-pyridyl)piperidines of general formula:

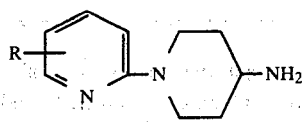

I in which R represents hydrogen; a halogen; a method group; a trifluoromethyl group; a lower alkoxy group; a trifluoromethoxy group; a 2,2,2-trifluoroethoxy group; a lower alkylthio group; a trifluoromethylthio group; a phenoxy group; a phenoxy group substituted by a halogen, a trifluoromethyl group, a lower alkyl, a lower alkoxy, a lower alkylthio or a cyano group; a phenylthio group; or a phenylthio group substituted in the phenylring by an atom of halogen, a trifluoromethyl group, a lower alkyl, a lower alkoxy, a lower alkylthio or a cyano group; and to the pharmaceutically acceptable salts thereof.

The terms "lower alkyl", "lower alkoxy" and "lower alkylthio", as used in the present specification, designate groups containing the residue of a saturated aliphatic hydrocarbon containing 1 to 3 atoms of carbon, namely methyl, ethyl, propyl and isopropyl.

The term "halogen" indicates one of the four common halogens, fluorine, chlorine and bromine being particularly preferred.

The pharmaceutically acceptable salts of the 4-amino-1-(2-pyridyl)piperidines of the present invention include the non-toxic salts derived from mineral or organic acids, salifying one or the two basic functions present in the molecule of the compounds of formula I hereinabove, such as hydrochlorides, hydrobromides, succinates, tartrates, citrates, fumarates, maleates, pamoates, napsylates, mesylates, tosylates.

German Pat. No. 738.495 describes a process for the preparation of 4-aminopiperidines having the following general formula:

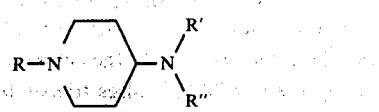

II in which R represents an aliphatic, aromatic, alicyclic or heterocyclic group and R' and R" represent hydrogen or alkyl groups.

The compounds of formula II are regarded as serving for therapeutic purposes; they show antispasmodic properties. Said patent describes 8'-[4-(dimethylamino)-piperidyl]quinoline, but it does not mention any aminopiperidine directly bonded to a heterocycle ring, in particular to a pyridine.

It has now been found that the novel aminopiperidines of formula I have a remarkable anorexiant activity and that they may therefore be used for treating obesity.

It has also been found that the anorexiant activity of the novel aminopiperidines of formula I is selective and therefore does not have any secondary effects on the central nervous system. In particular, the novel compounds of the present invention act on the central serotoninergic system without effect on the dopaminergic system and with a moderate action on the noradrenergic system.

According to the present invention, the novel 4-amino-1-(2-pyridyl)piperidines are prepared by reacting a 2-halopyridine of formula

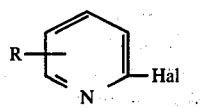

III in which R has the above-given significance and Hal represents an atom of halogen, with a blocked aminopiperidine of formula:

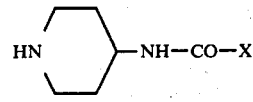

IV in which X represents an atom of hydrogen or a lower alkyl group and then by hydrolysing the N-substituted 4-amino-1-(2-pyridyl)piperidine thus obtained, of formula:

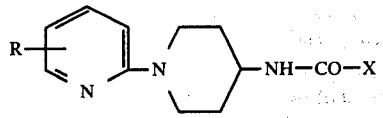

V in which R and X have the above-given significance, under acid or basic conditions.

The 4-acetamidopiperidine (formula IV, X=methyl) represents the preferred blocked 4-aminopiperidine.

The reaction of the 2-halopyridine of formula III with the blocked 4-aminopiperidine is conducted in an organic solvent such as an alcohol, n-butanol, n-pentanol or n-hexanol preferably, dimethylformamide, dimethylsulfoxide, sulfolane, acetonitrile, pyridine and the like, at a temperature of between 50° and 200° C. in the presence of an alkaline condensation agent, such as hydroxide, a carbonate or an alkaline bicarbonate. After 20 to 120 hours, the reaction is complete and the N-substituted 4-amino-1-(2-pyridyl)piperidine of formula V thus obtained is isolated in accordance with conventional techniques.

To accelerate the reaction, it may be expedient to operate in the presence of a catalyst, for example in the presence of copper.

The N-substituted 4-amino-1-(2-pyridyl) piperidines of formula V are novel intermediate products which constitute one of the aspects of the present invention.

The unblocking of the substituted amino group is effected in accordance with the well known techniques of acid or basic hydrolysis.

The acid hydrolysis is effected, for example, by heating the blocked 4-amino-1-(2-pyridyl)piperidine of formula V in an aqueous solution of a mineral or organic acid, preferably hydrochloric acid, and the 4-amino-1-(pyridyl)piperidine of formula I is isolated in accordance with conventional techniques.

Hydrolysis in a basic medium is effected by treatment of the compound of formula V with a mineral base, preferably sodium hydroxide. At the end of hydrolysis, the 4-amino-1-(2-pyridyl) piperidine is isolated and/or converted into its addition salts by treatment with an aqueous dilute alcoholic solution, or in an organic solvent of the salifying acid.

The blocked 4-aminopiperidines of formula IV employed as starting products may be prepared in accordance with known methods in the art, for example by catalytic reduction of the corresponding blocked 1-benzyl-4-aminopiperidines or by reduction of the corresponding blocked 4-aminopyridines.

The 4-acetamidopiperidine, preferred starting product, is described in U.S. Pat. No. 3,124,586.

The novel 4-amino-1-(2-pyridyl)piperidines of the present invention and salts thereof show a remarkable selective anorexiant activity without any action of the amphetaminic type. The selectivity of their action is demonstrated by the lack of secondary pharmacological activities, such as sedative or stimulating activity and the action inhibiting the locomotor activity.

The compounds of the present invention do not show any antispasmodic action nor undesirable secondary cardiovascular effects.

The compounds of formula I above, in which the substituent R is in the position 6 of the pyridine ring are particularly preferred.

With respect to their degree of activity, the 4-amino-1-(2-pyridyl)piperidines of the present invention are sparingly toxic and present a good therapeutic index. In Table I hereinbelow, the acute toxicity is expressed in the form of "zone of mortality". 6 batches of male mice weighing about 20 g were used, in which were injected the compounds of the present invention, dissolved or suspended in carboxymethylcellulose, by the intraperitoneal route, at at least four doses for each batch of animals. The animals were observed for 48 hours after the treatment and the number of deceased animals, as well as the type of death, were recorded. The "mortality zone" is represented by the doses at which the lowest mortality (at least 1 death) and the highest are observed.

The anorexiant activity was assessed by the food consumption method in the rat. Female rats weighing 200 g were used, trained for 10 days to eat during a period of 4 hours and selected on the eighth day. After the tenth day, the randomized animals were divided into a "control group", treated solely with the carrier, and into several "treated groups". The treatment was effected by the intraperitoneal route 30 minutes before the presentation of food and the quantity of food consumed in the course of the first hour was then measured. The data in Table I indicate the percentage of inhibition of the food consumption of the animals treated with the compounds according to the present invention with respect to the controls.

TABLE I

| Compound | Mortality zone mg/kg | FOOD CONSUMPTION | |
|---|---|---|---|
| | | dose (mg/kg) | % inhibition |
| CM 57227 (Example 1) | 100-150 | 10 | 70.8 |
| CM 57385 (Example 11) | 150-250 | 30 | 78.2 |
| CM 57371 (Example 10) | 175-225 | 40 | 77.2 |
| CM 57373 (Example 12) | 100-175 | 20 | 89.8 |
| CM 57369 (Example 9) | 150-200 | 40 | 95.2 |
| CM 57366 (Example 3) | 150-200 | 30 | 67.0 |

Table I shows that the compounds of the present invention, at doses of between about 1/10 and 1/5 of the minimum toxic dose in the mouse, show a remarkable decrease in the food consumption.

The anorexiant activity by the oral route of a product according to the present invention, 4-amino-1-(6-chloro-2-pyridyl)piperidine in the form of mono hydrochloride (CM 57227, compound of Example 1), was tested in accordance with the food consumption method described hereinabove; as well known anorexiant product, fenfluramine, as well as 1-(6-chloro-2-pyridyl)piperazine in the form of monohydrochloride, described in U.S. Pat. No. 4,078,063, and 1-(6-chloro-2-pyrazinyl) piperazine in monohydrochloride form, described in British Pat. No. 1,492,528, were used as reference products.

The products were also assessed as a function of their action on the locomotor activity in the rat. To this end, female rats weighing about 200 g were used, to which the compounds were administered by the oral route. After 30 minutes, the treated animals were placed in a cage (80×80 cm) provided with a photoelectric cell for measuring the spontaneous movements, and the number of pulses transmitted to the cell for 10 minutes was recorded. The inhibition of the locomotor activity of each substance (6 to 10 animals per dose) was expressed as a percentage with respect to the controls.

Table II shows:

the acute toxicity, expressed at $LD_{50}$ in the rat by the oral route (data A);

the anorexiant activity, expressed as oral dose inhibiting by 50% the food consumption ($ED_{50}$, data B);

the action on the locomotor activity, expressed as oral dose inhibiting by 50% the spontaneous motility, namely the number of pulses transmitted to the photoelectric cell during the 10 minutes ($ID_{50}$, data C);

the ratio between the acute toxicity and the anorexiant activity, which expresses the therapeutic index associated with the acute toxicity (data A/B);

the ratio between the action on the locomotor activity and the anorexiantactivity, which expresses the therapeutic index associated with the inhibition of the locomotor activity, sign of a secondary effect of the sedative or depressant type (data C/B).

TABLE II

| Compounds | A Acute toxicity LD$_{50}$ (mg/kg) | B anorexiant activity ED$_{50}$ (mg/kg) | C locom. act. inhibition ID$_{50}$ (mg/kg) | A/B | C/B |
|---|---|---|---|---|---|
| CM57227 (Ex. 1) | 190 | 7.8 | 60 | 24.3 | 7.7 |
| fenfluramine | 100.9 | 4.0 | 12 | 25.2 | 3.0 |
| 1-(6-chloro-2-pyridyl)piperazine HCl | 174 | 3.6 | 2.1 | 48.3 | 0.58 |
| 1-(6-chloro-2-pyrazinyl)piperazine HCl | 79.6 | 1.7 | 0.6 | 46.8 | 0.3 |

Table II shows that the product according to the present invention has the least toxicity, whilst retaining a high degree of anorexiant activity, and shows an inhibition of the locomotor activity only at doses about 8 times higher than the anorexiant ED$_{50}$. Reference compounds, 1-(6-chloro-2-pyridyl)piperazine and 1-(6-chloro-2-pyrazinyl)piperazine, which in the test employed are very active as anorexiants, inhibit the locomotor activity at doses even lower than the anorexiant ED$_{50}$, whilst the fenfluramine, whose therapeutic index A/B is almost equal to that of the 4-amino-1-(6-chloro-2-pyridyl)piperidine of the present invention, has a much greater inhibiting action on the locomotor activity.

From the biochemical point of view, the novel 4-amino-1-(2-pyridyl)piperidines of formula I and their salts prove to be remarkable inhibitors of the uptake of the serotonin also having a moderate inhibiting effect on the uptake of the noradrenaline and no inhibiting action on the uptake of dopamine, this comprising a selective activity on the cerebral amines and reduced secondary effects.

In particular, the compounds of the present invention, in vivo, do not cause any depletion of serotonin at central level. Table III below summarises the cerebral levels of serotonin after intraperitoneal administration in the rat of a compound according to the present invention, 4-amino-1-(6-chloro-2-pyridyl) piperidine in monohydrochloride form (CM 57227, product of Example 1). Fenfluramine was used as reference product.

TABLE III

| Compound | dose (mg/kg i.p.) | Cerebral levels of serotonin % with respect to controls |
|---|---|---|
| CM 57227 | 5 | 105 |
|  | 10 | 120 |
| fenfluramine | 3.75 | 69* |
|  | 7.5 | 51* |
|  | 15 | 42* |

*significant: $p < 0.01$

The animals were treated 60 minutes before sacrifice.

This Table shows that the product of the present invention, at anorexiant doses, does not modify the cerebral levels of serotonin, whilst fenfluramine, at equivalent doses, causes a significant reduction in cerebral serotonin already described in the art (Arch. Intern. Pharmacodyn. Ther. 1967, 170, 276).

As a lasting depletion of serotonin may be considered as a sign of potential neurotoxicity (C. D. Morgan et al. Life Sci. Part I, 11, 83;(1972), there is less possibility that the prolonged use of the compound according to the present invention provokes secondary effects at central level.

Due to their good anorexiant activity, their low toxicity with respect to the degree of activity and the absence of major secondary effects, the compounds of the present invention may be used as anorexiant agents at doses of 0.01 to 10 mg/kg per day. They may be administered by the oral, sublingual, subcutaneous, intramuscular, intravenous, transdermic or rectal route in pharmaceutical compositions containing from 0.5 to 250 mg of active ingredient per dosage unit, mixed with the conventional excipients. The preferred route of administration is the oral route, in the form of tablets, tablets with delayed effect, pills, sachets, suspensions, syrups.

The following example illustrate the invention without, however, limiting same.

EXAMPLE 1

A suspension of 175.5 g of 4-acetamidopiperidine, 269.7 g of potassium carbonate and 182.5 g of 2,6-dichloropyridine in 1600 ml of n.penytylic alcohol is heated at reflux with stirring for 40 hours. The reaction mixture is cooled, the solvent is removed under reduced pressure and the residue is taken up with 100 ml of water. The solid product is extracted with 2000 ml of methylene chloride, the organic phase is washed with water, it is dried over anhydrous sodium sulfate and evaporated to dryness. The residue is taken up with 1200 ml of diisopropylic ether, stirred for 30 minutes, filtered and washed with diisopropylic ether. 246 g of 4-acetamido-1-(6-chloro-2-pyridyl)piperidine are obtained; m.p. 153° to 155° C.

A solution of 245 g of 4-acetamido-1-(6-chloro-2-pyridyl)piperidine in 1220 ml of 6 N hydrochloric acid are heated at reflux for 8 hours. The reaction mixture is cooled and is concentrated under reduced pressure. The residue is treated with 4 N sodium hydroxide up to a clearly basic pH and the oil which separates is extracted with diethyl ether. The organic phase is washed with water, it is dried over anhydrous sodium sulfate and evaporated to dryness. The oily residue is poured, at 0° C., in 350 ml of concentrated hydrochloric acid, the solution thus obtained is decoloured with charcoal and the pH of the limpid solution is adjusted to 5. The solid which precipitates is filtered, it is washed three times with 50 ml of water and is crystallised in water by cooling to 3°–4° C. The product thus obtained is dried over $P_2O_5$ at 50° C. under reduced pressure. 200 g of monohydrochloride of 4-amino-1-(6-chloro-2-pyridyl) piperidine (CM 57227) are obtained, having a melting point of about 300° C. with decomposition.

EXAMPLE 2

Following the modus operandi described in Example 1, by reaction of 4-acetamidopiperidine with 2,3-dichloropyridine, 4-acetamido-2-(3-chloropyridyl)-piperidine is obtained, with a yield of 70%, which, after crystallization in ethyl acetate, melts at 118° to 120° C. By hydrolysis of the product thus obtained with 6 N hydrochloride acid, the monohydrochloride of 4-amino-1-(3-chloropyridyl)piperidine (CM 57375) is obtained which is crystallised in 90% ethanol; m.p. 258° to 260° C. with decomposition.

Yield: 67%

EXAMPLE 3

A mixture of 0.088 mole of 4-acetamidopiperidine, 15 g of potassium carbonate, 0.088 mole of 2-chloro-6-methoxypyridine in 100 ml of dimethylsulfoxide is heated with stirring to 130° C. for 50 hours, then it is cooled, the mixture is poured into water and the suspension thus obtained is extracted with diethyl ether. The aqueous phase is extracted with methylene chloride, the organic phase is washed with water, it is dried on anhydrous sodium sulfate and evaporated to dryness. 4-acetamido-1-(6-methoxy-2-pyridyl)piperidine is thus obtained which, after crystallisation in 95% ethanol, melts at 125° to 127° C.

Yield: 43% of the theoretical.

A solution of 10 g of 4-acetamido-1-(6-methoxy-2-pyridyl)piperidine, 44 g of sodium hydroxide pellets, 44 ml of water and 200 ml of ethylene glycol is heated at reflux for 20 hours, then is cooled, the reaction mixture is poured into water, the solution thus obtained is saturated with sodium chloride and extracted with diethyl ether. The organic phase is washed with a saturated aqueous solution of sodium chloride, it is dried over sodium sulfate and concentrated to dryness. The residual oil is dissolved in 160 ml of isopropanol and the solution thus obtained is treated with a solution of hydrochloric acid in isopropanol. The solid which separates if filtered, it is washed with isopropanol and recrystallised in ethanol. 8.5 g of monohydrochloride of 4-amino-1-(6-methoxy-2-pyridyl) piperidine (CM 57366) are obtained; m.p. 225° to 235° C. (with decomposition).

Yield: 87%.

EXAMPLE 4

A mixture of 12.5 g of 4-acetamidopiperidine, 15 g of potassium carbonate, 10 g of 2-chloropyridine in 100 ml of dimethylsulfoxide, is heated with stirring for 50 hours to 130° C., then it is cooled, poured into water and the suspension thus obtained is extracted with diethyl ether. The aqueous phase is extracted with methylene chloride, the organic phase is washed with water, it is dried over anhydrous sodium sulfate and evaporated to dryness. Thus, 4-acetamido-1-(2-pyridyl) piperidine is obtained which, after crystallisation in isopropanol and recrystallisation in ethyl acetate, melts at 165° to 168° C.

Yield: 4.7 g (24.5% of the theoretical).

By hydrolysis of the 4-acetamido-1-(2-pyridyl) piperidine thus obtained in the presence of 6 N hydrochloric acid according to the modus operandi described in Example 1, the dihydrochloride of 4-amino-1-(2-pyridyl) piperidine (CM 57359) is obtained; m.p.>260° C. (with decomposition).

Yield 72% of the theoretical.

EXAMPLE 5

A mixture of 0.116 moles of 2-chloro-6-phenoxypyridine, 21.5 g of anhydrous potassium carbonate, 0.151 moles of 4-acetamidopyridine and 0.118 mole of copper in powder form in 100 ml of sulfolane is heated to 150° C. with stirring for 40 hours. The sulfolane is distilled, the residue is taken up with water, the suspension is treated with water and it is extracted with methylene chloride. The organic phase is washed with water, dried and concentrated to dryness. By crystallisation of the residue in diisopropylic ether, 4-acetamido-2-(6-phenoxy-2-pyridyl)piperidine is obtained; m.p. 104° to 106° C.

Yield: 30% of the theoretical.

By hydrolysing the 4-acetamido-2-(6-phenoxy-2-pyridyl)piperidine thus obtained with sodium hydroxide, by pouring the reaction mixture in water and by treating it with hydrochloric acid as described in Example 3, the monohydrochloride of 4-amino-2-(6-phenoxy-2-pyridyl)piperidine (CM 57380) is obtained; m.p. 195° to 198° C.

Yield: 25% of the theoretical.

EXAMPLES 6 TO 8

Following the modus operandi described in Example 5, by reaction of the 4-acetamidopiperidine with 2-chloro-4-methylpyridine, 2-chloro-6-(methylthio) pyridine and 2-chloro-6-(isopropylthio)pyridine (b.p. 130° C./16 mm Hg, prepared by reaction of 2,6-dichloropyridine with the isopropylmercaptan salt of Na), the corresponding 4-acetamido-1-(2-pyridyl)-piperidines are obtained, which, by hydrolysis with sodium hydroxide, give the 4-amino-1-(2-pyridyl)-piperidines. The physicochemical characteristics and yields of the reactions are summarised in Table IV.

TABLE IV

| | Intermediate products | | | Final products | | |
|---|---|---|---|---|---|---|
| Ex. | Compounds | yield % | m.p. °C. | Compounds | yield % | m.p. °C. (dec.) |
| 6 | 4-acetamido-1-(4-methyl-2-pyridyl)piperidine | 48 | 156–159 | 4-amino-1-(4-methyl-2-pyridyl) piperidine 2HCl (CM 57377) | 74 | 340–345 |
| 7 | 4-acetamido-1-(6-methylthio-2-pyridyl)piperidine | 39 | 128–130 | 4-amino-1-(6-methylthio-2-pyridyl)piperidine HCl (CM 57390) | 64 | 258–260 |
| 8 | 4-acetamido-1-(6-isopropylthio-2-pyridyl)piperidine | 64 | 115–117 | 4-amino-1-(6-isopropylthio-2-pyridyl) piperidine. HCl (CM 57419) | 40 | 206–208 |

EXAMPLE 9

A mixture of 9.5 g of 2-chloro-6-(phenylthio) pyridine (b.p. 112° to 116° C./0.01 mm Hg, prepared by reaction of 2,6-dichloropyridine with the sodium salt of thiophenol), 7.8 g of potassium carbonate and 7.6 g of 4-acetamidopyridine in 75 ml of sulfolane is heated to 150° C. with stirring for 50 hours, then the sulfolane is concentrated to 1/5th of its volume, the mixture is poured in 100 ml of water and extraction is effected four times with 150 ml of diethyl ether. The organic phase is washed with water, dried over anhydrous sodium sulfate, concentrated to dryness and the residue is crystallised in 40 ml of ethyl acetate. 6.8 g of 4-acetamido-1-(6-phenylthio-2-pyridyl)piperidine are thus obtained; m.p. 110° to 112° C.

By hydrolysing the 4-acetamido-2-(6-phenylthio-2-pyridine)piperidine thus obtained with sodium hydroxide, by pouring the reaction mixture in water and by treating it with 6 N hydrochloric acid as described in Example 3, the monohydrochloride of 4-amino-1-(6-phenylthio-2-pyridyl)piperidine (CM 57369) is obtained which, after crystallisation in ethanol, melts at 245° to 247° C. with decomposition.

Yield: 57.5%.

EXAMPLE 10

0.042 mole of 2-chloro-6-methylpyridine, 0.056 mole of anhydrous potassium carbonate and 0.052 mole of 4-acetamidopyridine in 75 ml of sulfolane are heated to 150° C. with stirring for 24 hours, then the sulfolane is concentrated up to 1.5 of its volume, the mixture is poured into 100 ml of water and extraction is effected four times with 150 ml of diethyl ether. The organic phase is washed with water, it is dried over anhydrous sodium sulfate, concentrated to dryness and the residue is crystallised in 40 m of ethyl acetate. Thus, the 4-acetamido-1-(6-methyl-2-pyridyl)piperidine is obtained; m.p. 145° to 147° C.

Yield: 28%.

By hydrolysis of the 4-acetamido-1-(6-methyl-2-pyridyl)piperidine thus obtained in the presence of 6 N hydrochloric acid in accordance with the modus operandi described in Example 1, the dihydrochloride of 4-amino-1-(6-methyl-2-pyridyl)piperidine (CM 57371) is obtained, which, crystallised in 95% ethanol, melts at 308° to 310° C. with decomposition.

EXAMPLE 11

A mixture of 19 g of 2-chloro-6-(2,2,2-trifluoroethoxy)pyridine (b.p. 80° C./16 mm Hg, prepared by reaction of 2,6-dichloropyridine with 2,2,2-trifluoroethanolate of sodium), 14.87 g of 4-formamidopiperidine (m.p. 116° to 118° C., prepared by hydrogenation of 4-formamido-1-benzylpiperidine in the presence of palladium on charcoal), 17.27 g of anhydrous potassium carbonate, 5.67 g of copper in powder form in 110 ml of sulfolane is heated to 100° C. with stirring for 50 hours, then the sulfolane is distilled, the residue is taken up with water and the suspension thus obtained is extracted with methylene chloride. The organic phase is washed with water, it is dried over anhydrous sodium sulfate and evaporated to dryness. The residue, firstly crystallised in an 84/16 by volume mixture of water/ethanol and afterwards in diisopropylic ether, gives 9 g of 4-acetamido-1-[6-(2,2,2-trifluoro)ethoxy-2-pyridyl] piperidine; m.p. 92° to 95° C.

By heating the 4-acetamido-1-[6-(2,2,2-trifluoro)ethoxy-2-pyridyl]piperidine at reflux for 3 hours in an 0.5 N solution of hydrochloric acid and then operating as described in Example 1, the monohydrochloride of 4-amino-1-[6-(2,2,2-trifluoro)ethoxy-2-pyridyl] piperidine (CM 57385) is obtained which, after crystallation in ethanol, melts at 218° to 225° C. with decomposition.

Yield: 48.5% of the theoretical.

EXAMPLE 12

A mixture of 0.042 mole of 2,6-dibromopyridine, 0.056 mole of anhydrous potassium carbonate and 0.052 mole of 4-acetamidopiperidine in 75 ml of sulfolane is heated to 150° C. with stirring for 20 hours, then the sulfolane is concentrated to 1/5th of its volume, the reaction mixture is poured in 100 ml of water and extracted with diethyl ether (4×150 ml). The organic phase is washed with water, dried over anhydrous sodium sulfate, concentrated to dryness and the residue is crystallised in 40 ml of ethyl acetate. The 4-acetamido-1-(6-bromo-2-pyridyl)piperidine is thus obtained; m.p. 158° to 160° C.

Yield: 56% of the theoretical.

By hydrolysis of the 4-acetamido-1-(6-bromo-2-pyridyl)piperidine thus obtained with 6 N hydrochloric acid in accordance with the modus operandi of Example 1, the monohydrochloride of 4-amino-1-(6-bromo-2-pyridyl) piperidine (CM 57373) is obtained which, after crystallisation in 95% ethanol, melts at 305° to 308° C., with decomposition.

Yield: 73% of the theoretical.

EXAMPLE 13

A solution of 0.482 mole of 4-acetamido-1-(6-chloro-2-pyridyl)piperidine in 610 ml of 6 N hydrochloric acid is heated at reflux for 8 hours, then the reaction mixture is cooled and concentrated under reduced pressure. The residue is treated with 4 N sodium hydroxide up to a clearly basic pH and the oil which separates is extracted with diethyl ether. The organic phase is washed with water, dried over anhydrous sodium sulfate and evaporated to dryness. The oily residue is crystallised by diisopropylic ether. 4-amino-1-(6-chloro-2-pyridyl)piperidine is thus obtained; m.p. 36° to 38° C.

Yield: 72% of the theoretical.

A solution of 0.02 mole of 4-amino-1-(6-chloro-2-pyridyl)piperidine in acetone is treated with a solution of 0.02 mole of fumaric acid in acetone. The product which precipitates is filtered, washed with acetone and crystallised in 95% ethanol. The fumarate of 4-amino-1-(6-chloro-2-pyridyl)piperidine is thus obtained; m.p. 238° to 240° C. (decomposition).

In the same way, the maleate (m.p. 184° to 196° C.), the tartrate (m.p. 205° to 208° C.), the p-toluenesulfonate (m.p. 218° to 220° C.), the succinate (m.p. 218° to 220° C. with decomposition), the 2-naphthalenesulfonate (m.p. 232° to 236° C. with decomposition) and the hydrochloric crystallised in methanol, identical to the product of Example 1, are obtained.

What is claimed is:

1. 4-amino-1-(2-pyridyl)piperidine of the formula:

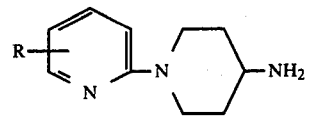

in which R represents chlorine; bromine; a trifuluoromethyl group; a trifluoromethoxy group; a 2,2,2-trifluoroethoxy group; a lower alkylthio group; a trifluoromethylthio group; a phenoxy group; a phenoxy group substituted in the phenyl ring by a halogen, a trifluoromethyl group, a lower alkyl group, a lower alkoxy group, a lower alkylthio group or a cyano group; a phenylthio group; a phenylthio group substituted in the phenyl ring by a halogen, a trifluoromethyl group, a lower alkyl group, a lower alkoxy group, a lower alkylthio group or a cyano group; or a pharmaceutically acceptable salt thereof.

2. 4-amino-1-(6-chloro-2-pyridyl)piperidine or a pharmaceutically acceptable salt thereof.

3. A monohydrochloride of 4-amino-1-(6-chloro-2-pyridyl) piperidine.

4. A dihydrochloride of 4-amino-1-[6-(2,2,2-trifluoro)ethoxy-2-pyridyl]piperidine.

5. A monohydrochloride of 4-amino-1-(6-bromo-2-pyridyl) piperidine.

6. A monohydrochloride of 4-amino-1-(6-phenylthio-2-pyridyl)piperidine.

7. 4-amino-1-(6-bromo-2-pyridyl)piperidine or a pharmaceutically acceptable acid addition salt thereof.

8. An anorectic pharmaceutical composition in dosage unit form comprising from 0.5 to 250 mg per dosage unit of a compound as claimed in claims 1 or 6 in admixture with a pharmaceutical carrier.

9. A composition as claimed in claim 8 which is formulated for oral administration.

10. N-substituted 4-amino-1-(2-pyridyl)piperidine of the formula:

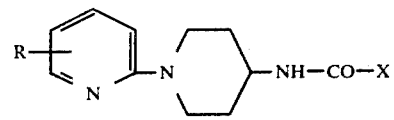

in which R represents hydrogen; a halogen; a methyl group; a trifluoromethyl group; a lower alkoxy group; a trifluoromethoxy group; a 2,2,2-trifluoroethoxy group; a lower alklylthio group; a trifluoromethylthio group; a phenoxy group; a phenoxy group substituted in the phenyl ring by a halogen, a trifluoromethyl group, a lower alkyl, a lower alkoxy, a lower alkylthio or a cyano group; a phenylthio group; a phenylthio group substituted in the phenyl ring by a halogen, a trifluoromethyl group, a lower alkyl group; a lower alkoxy group, a lower alkylthio group or a cyano group; and X represents an atom of hydrogen or a lower alkyl group.

11. 4-acetamido-1-(6-chloro-2-pyridyl)piperidine.

* * * * *

UNITED STATES PATENT AND TRADEMARK OFFICE
CERTIFICATE OF CORRECTION

PATENT NO. : 4,409,228
DATED : October 11, 1983
INVENTOR(S) : Dino Nisato and Paolo Carminati It is certified that error appears in the above-identified patent and that said Letters Patent are hereby corrected as shown below:

The title of the patent appearing as "ANDREXIANT AMINOPIPER-IDINES INTERMEDIATES THERETO AND DRUGS CONTAINING SAME" should read --ANOREXIANT AMINOPIPERIDINES INTERMEDIATES THERETO AND DRUGS CONTAINING SAME--.

Column 6, line 67, the word appearing as "hydrochloride" should read --hydrochloric--.

Column 8, line 66, the word appearing as "pyridine" should read --pyridyl--.

Column 10, line 39, the word appearing as "hydrochloric" should read --hydrochloride--.

Signed and Sealed this

Twentieth Day of December 1983

[SEAL]

Attest:

Attesting Officer

GERALD J. MOSSINGHOFF
Commissioner of Patents and Trademarks